United States Patent [19]

Murdock

[11] 4,278,605

[45] Jul. 14, 1981

[54] HETEROALKYLENEBISANTHRAQUINONES

[75] Inventor: Keith C. Murdock, Pearl River, N.Y.

[73] Assignee: American Cyanamid Company, Stamford, Conn.

[21] Appl. No.: 164,615

[22] Filed: Jun. 30, 1980

[51] Int. Cl.$^3$ ............................................. A01N 33/02
[52] U.S. Cl. ...................................... 260/367; 424/330
[58] Field of Search ....................... 260/367, 352, 379; 424/330

[56] References Cited

U.S. PATENT DOCUMENTS

| | | | |
|---|---|---|---|
| 2,913,465 | 11/1959 | Maier et al. | 260/367 |
| 4,027,021 | 5/1977 | Underwood | 424/330 |

FOREIGN PATENT DOCUMENTS

| | | | |
|---|---|---|---|
| 2734907 | 1/1979 | Fed. Rep. of Germany | 424/330 |
| 1195172 | 6/1970 | United Kingdom | 260/367 |

OTHER PUBLICATIONS

*Journal of Medicinal Chemistry*, vol. 22, p. 1024, Murdock et al., "Antitumor Agents 1,4-bis[(amino-alkyl)amino]-9,10-anthracenediones".

*Primary Examiner*—Patrick Garvin
*Assistant Examiner*—Raymond K. Covington
*Attorney, Agent, or Firm*—Edward A. Conroy, Jr.

[57] ABSTRACT

This disclosure describes novel heteroalkylenebisanthraquinones useful as chelating agents and for inhibiting the growth of transplanted mouse tumors.

16 Claims, No Drawings

HETEROALKYLENEBISANTHRAQUINONES

BRIEF SUMMARY OF THE INVENTION

This invention relates to new organic compounds and, more particularly, is concerned with novel heteroalkylenebisanthraquinones which may be represented by the following general formula:

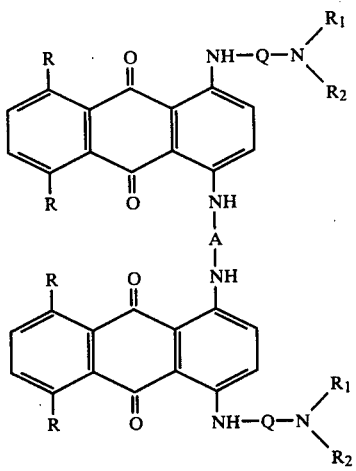

(I)

wherein Q is a divalent moiety selected from the group consisting of those of the formulae:

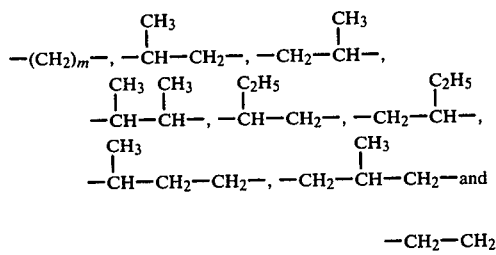

where m is an integer from 2 to 3, inclusive; A is $(CH_2)_nX(CH_2)_p$ where n and p may be the same or different and each may be an integer from 1 to 4 inclusive; X is selected from the group comprising

N, O, $(CH_2)_q$ where q is zero to 4,

where r is an integer from 2 to 6,

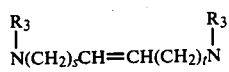

where s and t may be the same or different and each may be an integer from 1 to 3 and the olefin may be cis or trans, and

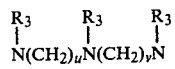

where u and v may be the same or different and each may be an integer from 2 to 5; R is hydrogen and hydroxy; $R_1$ and $R_2$ are each individually selected from the group consisting of hydrogen, alkyl having from 1 to 4 carbon atoms and monohydroxyalkyl having from 2 to 4 carbon atoms wherein the carbon atom alpha to the nitrogen atom may not bear a hydroxyl group. Suitable monohydroxyalkyl groups contemplated by the present invention are, for example, β-hydroxyethyl, β-hydroxypropyl, γ-hydroxypropyl and the like; $R_3$ is hydrogen and lower alkyl ($C_1$—$C_3$) and pharmaceutically acceptable acid-addition salts thereof.

Also included within the purview of the present invention are the leuco bases and tautomers thereof which may be represented by the following general formulae:

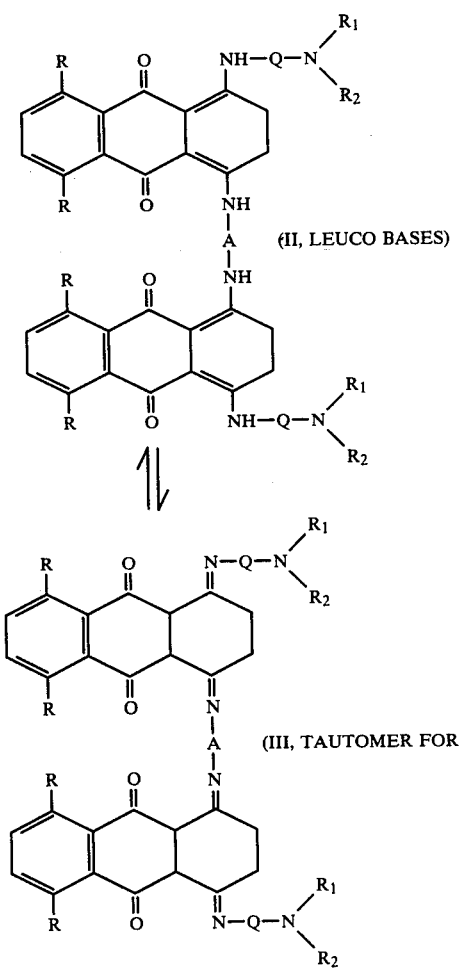

(II, LEUCO BASES)

(III, TAUTOMER FORM)

wherein Q, A, R, $R_1$, $R_2$ and $R_3$ are as hereinabove defined.

BACKGROUND OF THE INVENTION

K. C. Murdock, et al., J. Med. Chem., 22, 1024 (1979) have recently synthesized a group of 1,4-bis[(aminoalkyl)amino]anthraquinones which show anti-cancer activity in warm-blooded animals. Further investigation of some of these compounds indicates that they bind to deoxyribonucleic acid (DNA) by sandwiching between successive pairs of the nucleic acid bases of DNA [Johnson, et al., Cancer Treatment Reports, 63, 425 (1979)]. This type of insertion-binding of certain flat, polycyclic aromatic molecules to DNA is called intercalation and is also characteristic of some other drugs [Schwartz, Biomedicine, 24, 317 (1976)].

While the mechanism of action of the compounds described in the J. Med. Chem. reference vide supra, as well as the compounds of the current invention has not been verified, it is the inventors expectation that an anthraquinone nucleus with suitable basic side chains may intercalate into the DNA of cancer cells and thereby block their proliferation, and further, that two such anthraquinone systems, connected by suitable linking units, may intercalte into two positions of the same DNA chain, thereby enabling binding with greater strength and permanence. Alternatively, such double binding or bis-intercalation may link the adjacent strands of normally double stranded DNA and thereby prevent the separation of the strands, which is known to be required for DNA replication and cellular proliferation. Proliferation may also be impaired if one or both ends of such doubled anthraquinones are bound to other cellular components such as cell membranes, mitochondria, phospholipids or proteins.

While a biochemical mode of action has not been established, the following invention describes a series of bis-anthraquinones which substantially increase the life span of cancerous mice.

DETAILED DESCRIPTION OF THE INVENTION

The novel compounds of the present invention are obtainable as reddish-brown to blue-black solids having characteristic melting points and absorption spectra and which may be purified by leaching with lower alkanols since many of the free bases are insoluble in water and some of them are insoluble in most organic solvents. The organic bases of this invention (I, II, and III) form acid-addition salts with a variety of pharmacologically acceptable organic and inorganic salt-forming reagents. Thus acid-addition salts, formed by admixture of the organic free base with an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention, the free bases are equivalent to their acid-addition salts. The acid-addition salts of the organic bases of the present invention are solids. Most of them are relatively soluble in water, but all are relatively insoluble in non-polar organic solvents such as diethyl ether, benzene, toluene, and the like.

The novel compounds of the present invention may be prepared readily in accordance with the following reaction scheme:

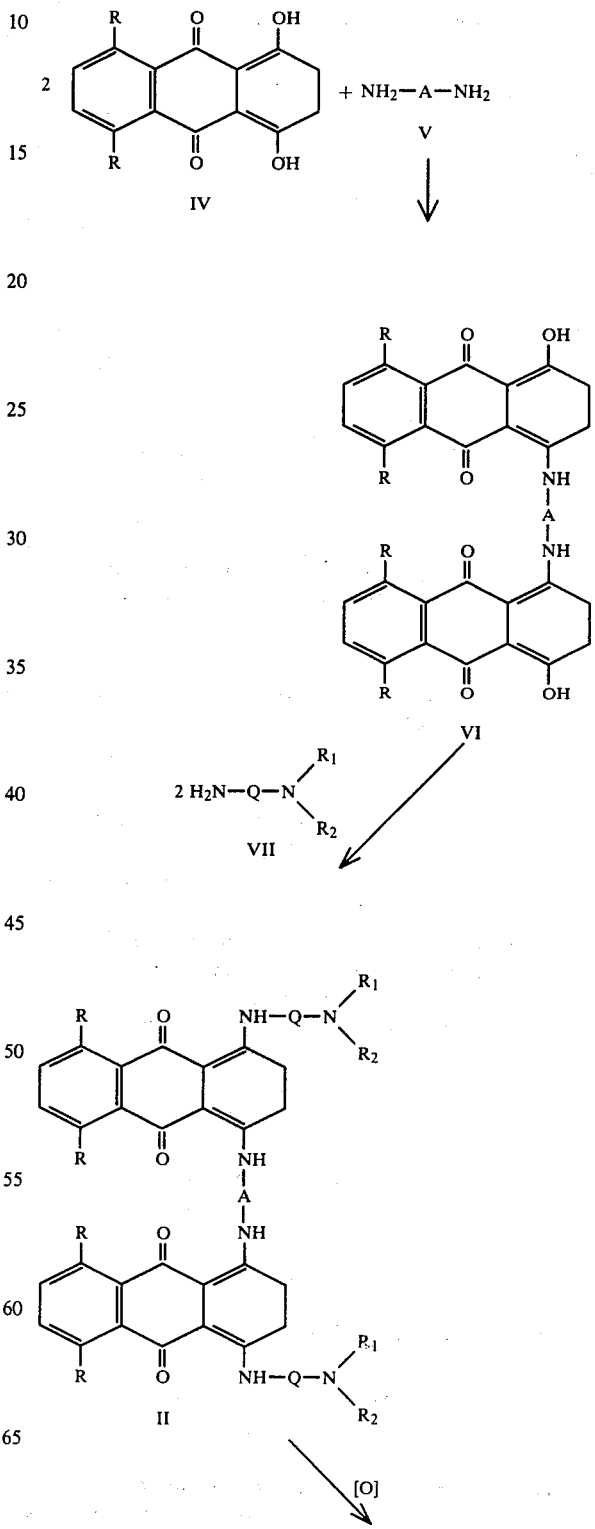

-continued

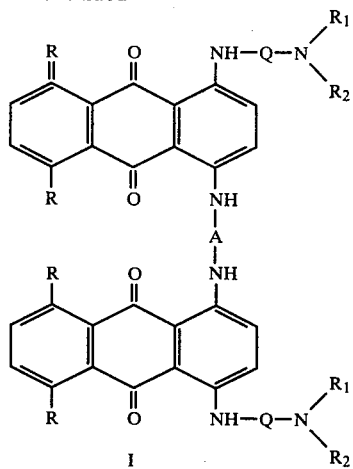

wherein R, $R_1$, $R_2$, A and Q are as hereinabove defined. In accordance with this reaction scheme, leuco 1,4,5,8-tetrahydroxyanthraquinone or leuco quinizarin (IV) is stirred with an appropriate heteroalkylenediamine (V) under nitrogen, in a solvent such as 2-methoxyethanol, ethanol, dimethylformamide and the like at from 5° C. to 50° C. for one to 15 hours to provide the corresponding 1,1'-bis leuco intermediate compound (IV). The intermediate (VI) in 2-methoxyethanol is condensed with an appropriate alkylenediamine (VII) at from about 40° C. to about 60° C. under an atmosphere of nitrogen for several hours to produce the corresponding leuco bases (II). Neither intermediate (VI) nor the leuco base (II) need be isolated. The leuco bases (II) may be readily oxidized to the fully aromatic derivatives (I) by a variety of methods such as air oxidation or treatment with hot nitrobenzene, or treatment with chloranil in acid, or with hydrogen peroxide, or sodium perborate. If a non-acidic oxidizing system is used, the cooled mixture is then acidified. Filtration gives a salt of the oxidized product (I). This salt may generally be purified by dissolving it in water, removing insoluble contaminates by centrifugation, then reprecipitating the salt by increasing the acidity to an acid value from 0.2 N to 0.8 N depending upon the example. (The purification is monitored by thin layer chromatography.) The salt is sedimented and washed with dilute acid by centrifugation, then washed by filtration with alcohol and/or acetone.

The novel compounds described herein are useful as chelating, complexing or sequestering agents. The complexes formed with polyvalent metal ions are particularly stable. These properties, of course, render them useful for a variety of purposes wherein metal ion contamination presents a problem; e.g., as stabilizers in various organic systems such as saturated and unsaturated lubricating oils and hydrocarbons, fatty acids and waxes, wherein transition metal ion contamination accelerates oxidative deterioration and color formation. They are further useful in analyses of polyvalent metal ions which may be complexed or extracted by these materials and as metal carriers. Other uses common to sequestering agents are also apparent for these compounds. In addition, the leuco bases (II) are useful as intermediates in the preparation of the fully aromatic derivatives (I).

The novel compounds of the present invention also possess the property of inhibiting the growth of transplanted mouse tumors as established by the following tests.

Lymphocytic leukemia P388 test

The animals used are DBA/2 mice all of one sex, weighing a minimum of 17 g. and all within a 3 g. weight range. There are 5 or 6 animals per test group. The tumor transplant is by intraperitoneal injection of 0.5 ml. of dilute ascitic fluid containing $10^6$ cells of lymphocytic leukemia P388. The test compounds are administered intraperitoneally on days one, 5 and 9 (relative to tumor inoculation) at various doses. The animals are weighed and survivors are recorded on a regular bases for 30 days. The median survival time and the ratio of survival time for treated (T)/control (C) animals are calculated. The positive control compound is 5-fluorouracil given as a 60 mg./kg. injection. The results of this test with representative compounds of the present invention appear in Table I. The criterion for efficacy is $T/C \times 100 \geq 125\%$.

TABLE I

| Lymphocytic Leukemia P388 Test | | | | |
|---|---|---|---|---|
| Compound | Dose (mg./kg.) | Median Survival Time (days) | T/C × 100 (percent) | "Cures"* |
| 1,1'-[Iminobis(ethyleneimino-ethylene-imino)]bis[5,8-dihydroxy-4-[[2-(2-hydroxyethylamino)ethyl]amino]anthraquinone] tetrahydrochloride | 50 | 23.5 | 204 | |
| | 25 | 29.5 | 257 | |
| | 12.5 | >30.0 | >261 | |
| | 6.25 | 23.0 | 200 | |
| | 3.12 | 28.5 | 248 | |
| | 1.56 | 19.5 | 170 | |
| | 0.78 | 18.0 | 156 | |
| Control | 0 | 11.5 | — | |
| 5-Fluorouracil | 60 | 19.0 | 165 | |
| 1,1'[Ethylenebis(iminoethyleneimino)]-bis[5,8-dihydroxy-4-[[2-(2-hydroxy-ethylamino)ethyl]amino]anthraquinone] tetrahydrochloride | 12.5 | 19.0 | 173 | |
| | 6.25 | 20.0 | 182 | |
| | 3.12 | 21.0 | 191 | |
| | 1.56 | 21.5 | 195 | |
| | 0.78 | 17.5 | 159 | |
| | 0.39 | 19.5 | .77 | |
| | 0.19 | 14.0 | 127 | |
| | 0.10 | 14.0 | 127 | |
| Control | 0 | 11.0 | — | |
| 5-Flurouracil | 60 | 22.5 | 205 | |
| 1,1'-(Octamethylenediimino)bis[5,8-dihydroxy-4-[[2-(2-hydroxyethylamino)-ethyl]amino]anthraquinone] dihydrochloride | 100 | 30.0 | 273 | |
| | 50 | 24.5 | 223 | |
| | 25 | 21.5 | 195 | |
| | 12.5 | 19.0 | 173 | |
| | 6.25 | 23.5 | 214 | |

TABLE I-continued

Lymphocytic Leukemia P388 Test

| Compound | Dose (mg./kg.) | Median Survival Time (days) | T/C × 100 (percent) | "Cures"* |
|---|---|---|---|---|
| | 3.12 | 19.0 | 173 | |
| | 1.56 | 17.5 | 159 | |
| | 0.78 | 16.5 | 150 | |
| Control | 0 | 11.0 | — | |
| 5-Fluorouracil | 60 | 22.5 | 205 | |
| 1,1'-[Iminobis(ethyleneimino)]bis[5,8-dihydroxy-4-[[2-(2-hydroxyethylamino)-ethyl]amino]anthraquinone] trihydrochloride | 50 | >30.0 | >273 | |
| | 25 | >30.0 | >273 | |
| | 12.5 | 22.0 | 200 | |
| | 6.25 | 24.5 | 223 | |
| | 3.12 | 27.0 | 245 | |
| | 1.56 | 20.0 | 182 | |
| | 0.78 | 20.0 | 182 | |
| Control | 0 | 11.0 | — | |
| 5-Fluorouracil | 60 | 22.5 | 205 | |
| 1,1'-[Trimethylenebis(iminoethyleneimino)]bis[5,8-dihydroxy-4-[[2-(2-hydroxyethylamino)ethyl]amino]anthraquinone] tetrahydrochloride | 200 | 20.0 | 174 | |
| | 100 | 36.0 | 313 | 1/6 |
| | 50 | 26.0 | 226 | |
| | 25 | 32.5 | 283 | 1/6 |
| | 12.5 | 22.5 | 196 | |
| | 6.25 | 23.0 | 200 | |
| | 3.12 | 21.0 | 183 | |
| | 1.56 | 20.5 | 178 | |
| | 0.78 | 18.0 | 156 | |
| Control | 0 | 11.5 | — | 0/6 |
| 5-Fluorouracil | 60 | 19.0 | 165 | — |
| 1,1'-[2-Butenylenebis(iminoethyleneimino)]bis[5,8-dihydroxy-4-[[2-(2-hydroxyethylamino)ethyl]amino]anthraquinone] tetrahydrochloride | 50 | 22.0 | 191 | |
| | 25 | >30.0 | >261 | |
| | 12.5 | 24.0 | 209 | |
| | 6.25 | 22.0 | 191 | |
| | 3.12 | 21.5 | 187 | |
| | 1.56 | 21.5 | 187 | |
| | 0.78 | 22.5 | 196 | |
| Control | 0 | 11.5 | — | |
| 5-Fluorouracil | 60 | 19.0 | 165 | |
| 1,1'-[Tetramethylenebis(iminoethyleneimino)]bis[5,8-dihydroxy-4-[[2-(2-hydroxyethylamino)ethyl]amino]anthraquinone] tetrahydrochloride | 12.5 | 16.5 | 138 | |
| | 6.25 | 19.0 | 158 | |
| | 3.12 | 20.0 | 167 | |
| | 1.56 | 18.5 | 154 | |
| | 0.78 | 18.0 | 150 | |
| Control | 0 | 12.0 | — | |
| 5-Fluorouracil | 60 | 21.0 | 175 | |
| 1,1'-[Tetramethylenebis(iminotrimethyleneimino)]bis[5,8-dihydroxy-4-[[2-(2-hydroxyethylamino)ethyl]amino]anthraquinone] tetrahydrochloride | 50 | >30.0 | >261 | 2/6 |
| | 25 | >30.0 | >261 | 2/6 |
| | 12.5 | 27.5 | 239 | 1/6 |
| | 6.25 | 21.5 | 187 | |
| | 3.12 | 22.0 | 191 | |
| | 1.56 | 19.0 | 165 | |
| | 0.78 | 22.5 | 196 | |
| Control | 0 | 11.5 | — | 0/6 |
| 5-Fluorouracil | 60 | 23.0 | 200 | — |
| 1,1'-[Ethylenebis(iminoethyleneimino)]-bis[5,8-dihydroxy-4-[(2-methylaminoethyl)amino]anthraquinone] tetrahydrochloride | 50 | 24.0 | 200 | |
| | 25 | 23.0 | 192 | |
| | 12.5 | 22.0 | 183 | |
| | 6.25 | 20.0 | 167 | |
| | 3.12 | 21.5 | 179 | |
| | 1.56 | 18.5 | 154 | |
| | 0.78 | 18.5 | 154 | |
| Control | 0 | 12.0 | — | |
| 5-Fluorouracil | 60 | 24.5 | 204 | |
| 1,1'-[Ethylenebis(iminoethyleneimino)]-bis[4-[[2-(2-hydroxyethylamino)ethyl]-amino]anthraquinone] tetrahydrochloride | 25 | 22.5 | 188 | |
| | 12.5 | 21.0 | 175 | |
| | 6.25 | 19.5 | 163 | |
| | 3.12 | 18.0 | 150 | |
| | 1.56 | 17.0 | 142 | |
| | 0.78 | 15.0 | 125 | |
| Control | 0 | 12.0 | — | |
| 5-Fluorouracil | 60 | 24.5 | 204 | |
| 1,1'-(Ethylenediimino)bis[4-(2-aminoethyl)amino]-5,8-dihydroxyanthraquinone dihydrochloride | 200 | 20.0 | 182 | 0/5 |
| | 100 | 20.0 | 182 | 0/5 |
| | 50 | 18.0 | 164 | 0/5 |
| | 25 | 18.0 | 164 | 0/5 |
| | 12 | 16.0 | 145 | 0/5 |
| | 6 | 18.0 | 164 | 0/5 |
| Control | — | 11.0 | — | 0/10 |
| 5-Fluorouracil | 60 | 17.0 | 155 | 0/10 |

*"Cures" = number of survivors/total at 60 days.

Melanotic melanoma B16

TABLE II

Melanotic Melanoma B16 Test

| Compound | Dose (mg./kg.) | Median Survival Time (days) | T/C × 100 (percent) | "Cures"* |
|---|---|---|---|---|
| 1,1'-[Iminobis(ethyleneimino-ethylene-imino)]bis[5,8-dihydroxy-4-[[2-(2-hydroxyethylamino)ethyl]amino]anthraquinone] tetrahydrochloride | 12 | 53 | 342 | |
| | 6.0 | 49.5 | 319 | |
| | 3.0 | 34.5 | 223 | |
| | 1.5 | 32.0 | 206 | |
| | 0.5 | 23.0 | 148 | |
| Control | 0 | 15.5 | — | |
| 5-Fluorouracil | 20 | 25.0 | 125 | |
| 1,1'-[Ethylenebis(iminoethyleneimino)]bis[5,8-dihydroxy-4-[[2-(2-hydroxyethyl-amino)ethyl]amino]anthraquinone] tetrahydrochloride | 14.5 | >35.0 | >219 | |
| | 25 | 35.0 | 219 | |
| | 12 | 29.5 | 184 | |
| | 6.0 | 32.0 | 200 | |
| | 3.0 | 33.0 | 206 | |
| | 1.5 | 28.0 | 175 | |
| | 0.75 | 22.0 | 137 | |
| | 0.25 | | | |
| Control | 0 | 16.0 | — | |
| 5-Fluorouracil | 20 | 25.0 | 156 | |
| 1,1'-(Octamethylenediimino)bis[5,8-dihydroxy-4-[[2-(2-hydroxyethylamino)-ethyl]amino]anthraquinone] dihydrochloride | 50 | >42.0 | >262 | |
| | 25 | 41.5 | 259 | |
| | 12 | 37.0 | 231 | |
| | 6.0 | 31.0 | 194 | |
| | 3.0 | 26.5 | 166 | |
| | 1.5 | 24.0 | 150 | |
| | 0.5 | 21.0 | 131 | |
| Control | 0 | 16.0 | — | |
| 5-Fluorouracil | 20 | 25.0 | 128 | |
| 1,1'-[Iminobis(ethyleneimino)]bis[5,8-dihydroxy-4-[[2-(2-hydroxyethylamino)-ethyl]amino]anthraquinone] tetrahydrochloride | 12 | >60.0 | >375 | 8/10 |
| | 6.0 | 49.5 | 309 | 4/10 |
| | 3.0 | 48.5 | 303 | 3/10 |
| | 1.5 | 35.0 | 219 | |
| | 0.5 | 25.0 | 156 | |
| Control | 0 | 16.0 | — | |
| 5-Fluorouracil | 20 | 25.0 | 128 | |
| 1,1'-[Trimethylenebis(iminoethylene-imino)]bis[5,8-dihydroxy-4-[[2-(2-hydroxyethylamino)ethyl]amino]anthraquinone] tetrahydrochloride | 50 | >60 | >387 | 8/10 |
| | 25 | >60 | >387 | 6/10 |
| | 12 | >60 | >387 | 6/10 |
| | 6.0 | 44 | 238 | |
| | 3.0 | 34 | 206 | |
| | 1.5 | 33 | 200 | |
| Control | 0 | 16.5 | — | |
| 5-Fluorouracil | 20 | 28.5 | 173 | |
| 1,1'-Butenylenebis(iminoethyleneimino)]-bis[5,8-dihydroxy-4-[[2-(2-hydroxyethyl-amino)ethyl]amino]anthraquinone] tetrahydrochloride | 12 | 47 | 303 | |
| | 6 | 31 | 200 | |
| | 3 | 39 | 252 | |
| | 1.5 | 33 | 213 | |
| | 0.5 | 27 | 174 | |
| Control | 0 | 15.5 | — | |
| 5-Fluorouracil | 20 | 25 | 161 | |
| 1,1'-Tetramethylenebis(iminoethylene-imino]bis[5,8-dihydroxy-4-[[2-(2-hydroxyethylamino)ethyl]amino]anthraquinone] tetrahydrochloride | 3.0 | 29 | 181 | |
| | 1.5 | 33 | 206 | |
| | 0.5 | 30 | 187 | |
| Control | 0 | 16 | — | |
| 5-Fluorouracil | 20 | 26 | 140 | |
| 1,1'-[Tetramethylenebis(iminotrimethyl-eneimino)]bis[5,8-dihydroxy-4-[[2-(2-hydroxyethylamino)ethyl]amino]anthraquinone] tetrahydrochloride | 12 | 35.5 | 222 | |
| | 6 | 30 | 187 | |
| | 3 | 37.5 | 234 | |
| | 1.5 | 28.5 | 178 | |
| | 0.5 | 23 | 144 | |
| Control | 0 | 16 | — | |
| 5-Fluorouracil | 20 | 26 | 140 | |
| 1,1'-[Ethylenebis(iminoethyleneimino)]-bis[5,8-dihydroxy-4-[(2-methylamino-ethyl)amino]anthraquinone] tetrahydrochloride | 25 | 33.0 | 206 | |
| | 12 | 43.5 | 272 | |
| | 6.0 | 45.0 | 281 | |
| | 3.0 | 36.0 | 225 | |
| Control | 0 | 18.0 | — | |
| 5-Fluorouracil | 20 | 26.0 | 127 | |
| 1,1'-[Ethylenebis(iminoethyleneimino)]-bis[4-[[2-(2-hydroxyethylamino)ethyl]-amino]anthraquinone] tetrahydrochloride | 12 | 53 | 342 | |
| | 6 | 49.5 | 319 | |
| | 3 | 34.5 | 223 | |
| | 1.5 | 32 | 206 | |
| | 0.5 | 23 | 148 | |
| Control | 0 | 15.5 | — | |
| 5-Fluorouracil | 20 | 25 | 161 | |
| 1,1'-(Ethylenediimino)bis[4-(2-aminoethyl)amino]-5,8-dihydroxyanthraquinone dihydrochloride | 50 | 31.0 | 177 | 1/10 |
| | 25 | 41.0 | 234 | 2/10 |
| | 12 | 41.0 | 234 | 3/10 |
| | 6 | 16.5 | 94 | 0/10 |
| | 3 | 37.5 | 214 | 0/10 |

TABLE II-continued

| Compound | Melanotic Melanoma B16 Test | | | |
| --- | --- | --- | --- | --- |
| | Dose (mg./kg.) | Median Survival Time (days) | T/C × 100 (percent) | "Cures"* |
| | 1.5 | 25.0 | 143 | 0/10 |
| Control | — | 14.5 | | 0/10 |
| 5-Fluorouracil | 20 | 26.0 | 149 | 0/10 |

"Cures" = number of survivors/total at 80 days.

Also embraced within the purview of the present invention are therapeutic compositions of matter useful for ameliorating cancer diseases in mammals and containing certain heteroalkylenebisanthraquinones (or the leuco bases and acid-addition salts thereof) which may be represented by the following structural formula:

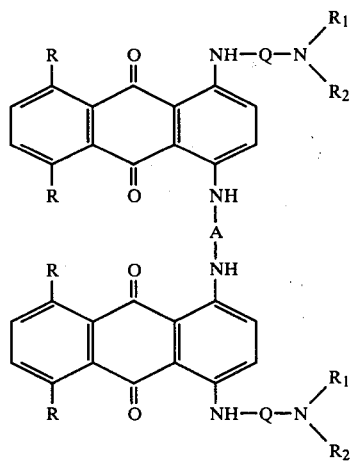
(I)

wherein Q is a divalent moiety selected from the group consisting of those of the formulae:

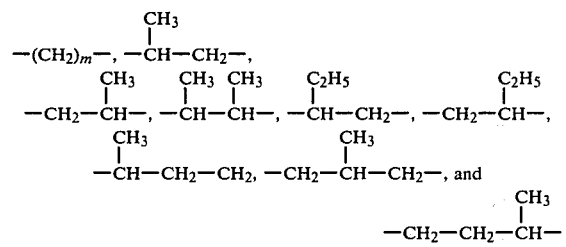

where m is an integer from 2 to 3, inclusive; A is $(CH_2)_nX(CH_2)_p$ where n and p may be the same or different and may be an integer from 1 to 4 inclusive; X is selected from the group comprising

O, $(CH_2)_q$ where q is 0 to 4,

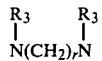

where r is an integer from 2 to 6,

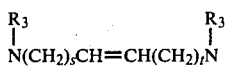

where s and t may be the same or different and may be an integer from 1 to 3 and the olefin may be cis or trans and

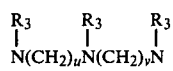

where u and v may be the same or different and may be an integer from 2 to 5; R is hydrogen and hydroxy; $R_1$ and $R_2$ are each individually selected from the group consisting of hydrogen, alkyl having from 1 to 4 carbon atoms and monohydroxyalkyl having from 2 to 4 carbon atoms wherein the carbon atom alpha to the nitrogen atom may not bear an hydroxy group. Suitable monohydroxyalkyl groups contemplated by the present invention are, for example, β-hydroxyethyl, β-hydroxypropyl, γ-hydroxypropyl and the like and $R_3$ is hydrogen and lower alkyl ($C_1$-$C_3$). This aspect of the invention includes the novel compositions of matter and the method of inducing the regression and/or palliation of leukemia and related cancers in mammals therewith.

The active ingredients of the therapeutic compositions and the novel compounds of the present invention inhibit transplanted mouse tumor growth and induce regression and/or palliation of leukemia and related cancers in mammals when administered in amounts ranging from about 5 mg. to about 200 mg. per kilogram of body weight per day. A preferred dosage regimen for optimum results would be from about 5 mg. to about 50 mg. per kilogram of body weight per day, and such dosage units are employed that a total of from about 350 mg. to about 3.5 g. of the active compound for a subject of about 70 kg. of body weight are administered in a 24 hour period. This dosage regimen may be adjusted to provide the optimum therapeutic response. For example, several divided doses may be administered daily of the dose may be proportionally reduced as indicated by the exigencies of the therapeutic situation. A decided practical advantage is that the active compound may be administered in any convenient manner such as by the intraveneous, intramuscular, or subcutaneous routes.

The active compounds may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 400 mg., with from about one to about 30 mg. being preferred. Expressed in proportions, the active compound is generally present in from about 0.1 to about 400 mg./ml. of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 to 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

This invention will be described in greater detail in conjunction with the following specific examples.

EXAMPLE 1

1,1'-[Iminobis(ethyleneimino-ethyleneimino)]bis[5,8-dihydroxy-4-[[2-(2-hydroxyethylamino)ethyl]amino]-anthraquinone]tetrahydrochloride 2-Methoxyethanol (280 ml.) is deaerated by bubbling in nitrogen for 15 minutes with stirring, then 10.97 g. (0.04 mole) of leuco 1,4,5,8-tetrahydroxyanthraquinone is added and stirring under nitrogen is continued at 25° C. for one hour. The mixture is chilled for 5 minutes in an ice bath, then 3.786 g. (0.02 mole) of redistilled tetraethylenepentamine (fractionated in a spinning brush column; b.p. 185° C. at 5 mm.) is added dropwise to the stirred mixture under nitrogen from a hypodermic syringe during a 7 minute period. The mixture is stirred for 3 hours as the temperature increases from 5°–22° C., then is placed in an unheated oil bath. Stirring under nitrogen is continued as the temperature of the bath is gradually raised to 50° C. and the mixture is then heated at 50° C. for another 3 hours. 2-(2-Aminoethylamino)ethanol (4.166 g., 0.04 mole) is added to the mixture with a hypodermic syringe. Stirring and heating under nitrogen is continued for 15 hours. The reaction mixture is allowed to cool. The resulting suspension of the leuco form of the product is oxidized by adding 10.01 g. (0.0403 mole) of chloranil, chilling the mixture in an ice bath during the dropwise addition of 25.0 ml. of 8 N ethanolic hydrogen chloride, then stirring for 15 hours without further cooling. The resulting mixture is centrifuged and the solid is washed 3 times with tetrahydrofuran by filtration to give 20.19 g. of a dark blue solid. The solid is stirred for 15 hours at room temperature with 360 ml. of water. The solution is centrifuged for 30 minutes at 17,000 G, then is decanted and filtered. The product is reprecipitated from the filtrate by acidifying to an acidity of 0.2 N by adding 5.9 ml. of 12.2 N hydrochloric acid. The mixture is centrifuged at 18,000 G for 25 minutes. The resulting solid is washed twice with 350 ml. portions of 0.2 N hydrochloric acid by dispersion with a high speed stirrer followed by centrifugation at 17,000 G, then is washed three times with ethanol by filtration to give 8.56 g. of the product of the Example as a dark blue solid; U.V. ($H_2O$, 10.31 mcg./ml.) 240 nm ($\epsilon$60,200), 275 (20,400), 564 sh ((17,400), 609 (28,100), 660 sh (20,400). A sample observed with a hot-stage microscope was unmelted by 350° C. Thin layer chromatography on silica gel with 0.2 M aqueous citric acid, acetonitrile and acetic acid in a volume ratio of 60:40:5 showed the product at Rf 0.0 and showed none of another antineoplastic compound which is a possible by-product from the above synthesis, 5,8-dihydroxy-1,4-bis-[2-[2-(2-hydroxyethyl)amino]ethyl]amino-9,10-anthracenedione dihydrochloride (Rf 0.4). The latter compound (Murdock, et al., loc. cit.), unlike the present product, is not precipitated from aqueous solution by adding even an equal volume of 12 N hydrochloric acid.

EXAMPLE 2

Leuco 1,1'-[Iminobis(ethyleneimino-ethyleneimino)]bis-[5,8-dihydroxy-4-[[2-(2-hydroxyethylamino)ethyl]amino]-anthraquinone]

The procedure of Example 1 is repeated except that the leuco form of the product is not acidified or oxidized with chloranil, but is directly collected by centrifugation and washed with ethanol to give the title compound as a red-brown solid.

EXAMPLE 3

1,1'-[Ethylenebis(iminoethyleneimino)bis[5,8-dihydroxy-4-[[2-(2-hydroxyethylamino)ethyl]amino]anthraquinone]tetrahydrochloride The procedure of Example 1 is used with 2.925 g. of triethylenetetramine rather than tetraethylenepentamine, affording 1.86 g. of the desired product as a blue-black solid, m.p. >350° C.

EXAMPLE 4

1,1'-(Octamethylenediimino)bis[5,8-dihydroxy-4-[[2-(2-hydroxyethylamino)ethyl]amino]anthraquinone]dihydrochloride The condensation and oxidation procedures of Example 1 are modified by replacing the tetraethylenepentamine with a solution of 2.88 g. of 1,8-diaminooctane in 10 ml. of 2-methoxyethanol. The oxidized mixture is centrifuged and the sedimented solid is washed 3 times with tetrahydrofuran by filtration. The product is essentially insoluble in water. It is suspended in 400 ml. of 0.6 N hydrochloric acid and centrifuged at 18,000 g. The pellet is dispersed and washed three times with 1 N hydrochloric acid by centrifugation at 17,000 G, then is washed with ethanol by centrifugation and finally is washed with acetone by filtration to give 11.08 g. of the product of the Example as a blue-black solid, m.p. 180°–185° C.

EXAMPLE 5

1,1'-[Iminobis(ethyleneimino)]bis[5,8-dihydroxy-4-[[2-(2-hydroxyethylamino)ethyl]amino]anthraquinone]-trihydrochloride With 2.06 g. of diethylenetriamine rather than tetraethylenepentamine the condensation and oxidation procedures of Example I gives 17.15 g. of the title compound as a blue-black solid which sinters above 215° C. It is essentially insoluble in water.

EXAMPLE 6

1,1'-[Trimethylenebis(iminoethyleneimino)]bis[5,8-dihydroxy-4-[[2-(2-hydroxyethylamino)ethyl]amino]anthraquinone]tetrahydrochloride The procedure of Example 1 is modified by using 3.20 g. of N,N'-bis(2-aminoethyl)-1,3-propanediamine (fractionated: b.p. 190° C. at 50 mm.) instead of tetraethylenepentamine. The product is 1.93 g. of a blue-black solid, m.p. >350° C.

EXAMPLE 7

1,1'-[2-Butenylenebis(iminoethyleneimino)]bis[5,8-dihydroxy-4-[[2-(2-hydroxyethylamino)ethyl]amino]anthraquinone]tetrahydrochloride The condensation and oxidation procedures of Example 1 are modified by using 3.44 g. of N,N'-bis(2-aminoethyl)-2-butene (fractionated: b.p. 169° C. at 5 mm.) instead of tetraethylenepentamine. The crude oxidation product is 11.81 g. of a blue-black solid. The solid in 360 ml. of water is stirred for 15 hours. The solution is centrifuged at 18,000 G, decanted and filtered. The filtrate is acidified to 0.2 N with 5.9 ml. of 12.3 N hydrochloric acid and the resulting flocculant suspension is centrifuged at 18,000 G. The supernatant is decanted and filtered. The filtrate is acidified to 0.4 N with 5.9 ml. of 12.3 N hydrochloric acid and is centrifuged. The supernatant is decanted and the residual solid is washed three times with ethanol to give 1.61 g. of the product of the Example as a dark blue solid, m.p. >350° C.

EXAMPLE 8

1,1'-[Tetramethylenebis(iminoethyleneimino)]bis[5,8-dihydroxy-4-[[2-(2-hydroxyethylamino)ethyl]amino]-anthraquinone]tetrahydrochloride A solution of 12.00 g. of fractionally distilled N,N'-bis(2-aminoethyl)-2-butene-1,4-diamine (b.p. 169° C. at 5 mm.) in 100 ml. of ethanol is shaken with 2.00 g. of Raney nickel catalyst for 4 hours at 19° C. in a Parr hydrogenator at an initial hydrogen pressure of 60 p.s.i. The solution is filtered, then fractionally diytilled in a spinning brush column, giving 9.19 g. of N,N'-bis(2-aminoethyl)-1,4-butanediamine, b.p. 161°–162° C. at 5 mm.

With 3.49 g. of this polyamine instead of tetraethylenepentamine the procedure of Example 1 gives 2.91 g. of the title compound as a dark blue solid which sinters slightly from 205° C., but is unmelted by 350° C.

EXAMPLE 9

1,1'-[Tetramethylenebis(iminotrimethyleneimino)bis-[5,8-dihydroxy-4-[[2-(2-hydroxyethylamino)ethyl-]amino]anthraquinone]tetrahydrochloride The procedure of Example 1 is used on half that scale, substituting 2.02 g. of spermine for tetraethylenepentamine. The desired product is obtained as 1.87 g. of a dark blue solid which melts from about 190°–199° C.

EXAMPLE 10

1,1'-[Hexamethylenebis(iminoethyleneimino)]bis[5,8-dihydroxy-4-[[2-(2-hydroxyethylamino)ethyl]amino]-anthraquinone]tetrahydrochloride Replacing the tetraethylenepentamine in the procedure of Example 1 with 4.05 g. of N,N'-bis(2-aminoethyl)-1,6-hexanediamine [van Alphen, Rec. Trav. Chim., 59, 31 (1940)] gives the title compound as a dark blue solid.

EXAMPLE 11

1,1'-[Oxybis(tetramethyleneimino)]bis[5,8-dihydroxy-4-[[2-(2-hydroxyethylamino)ethyl]amino]anthraquinone]-dihydrochloride 4,4'-Oxybis-1-butaneamine, 3.20 g., [Kimura, et al., Chem. Abstr., 60, 15988c (1964)] is used instead of tetraethylenepentamine in the procedure of Example 1 to give the desired product as a dark blue solid.

EXAMPLE 12

1,1'-[Ethylenebis(iminoethyleneimino)]bis[5,8-dihydroxy-4-[(2-methylaminoethyl)amino]anthraquinone]-tetrahydrochloride Fractionally distilled triethylenetetramine 2.92 g. (b.p. 140° C./5 mm., $n_D^{20}$ 1.4981), and 2.96 g. of N-methylethylenediamine are used in the procedure of Example 1 instead of tetraethylenepentamine and 2-(2-aminoethylamino)-ethanol, respectively. Effective reprecipitation of the product from the aqueous extract is achieved by acidification to 0.4 N with 11.8 ml. of 12.3 N hydrochloric acid followed by centrifugation at 17,000 G. The resulting solid is washed twice by centrifugation with 150 ml. portions of 0.4 N hydrochloric acid, once by filtration with ethanol and twice by filtration with acetone to yield 6.50 g. of the desired product as a dark blue solid, m.p. >350° C.; U.V. (H$_2$O, 9.31 mcg./ml.) λ max 235 nm (ϵ56,300), 274 sh (19,800), 608 (23,600), 658 sh (15,100).

EXAMPLE 13

1,1'-[Ethylenebis(iminoethyleneimino)]bis[4-[[2-(2-hydroxyethylamino)ethyl]amino]anthraquinone]tetrahydrochloride Fractionally distilled triethylenetetramine, 2.92 g. (b.p. 140° C. at 5 mm., $n_D^{20°}$ C. 1.4981), and 9.69 g. of leucoquinizarin are used in the procedure of Example 1 in place of tetraethylenepentamine and leuco 1,4,5,8-tetrahydroxyanthraquinone, respectively. The aqueous extract of the crude oxidized product is acidified to 0.4 N with 11.8 ml. of 12.3 N hydrochloric acid and then is centrifuged at 17,000 G. The supernatant solution is decanted and filtered. The filtrate is acidified to 0.8 N with 11.8 ml. of 12.3 N hydrochloric acid and is centrifuged as above. The supernatant solution is decanted and the residue is washed twice by centrifugation with 50.0 ml. portions of 0.8 N hydrochloric acid, then is washed three times with ethanol by filtration to give 2.61 g. of the product of the Example as a purple-black solid, m.p. 175°–180° C.; U.V. (H$_2$O, 12.36 mcg./ml.) λ max 253 nm (ϵ56,300), 327 (9,000), 552 sh (15,400), 582 (18,400), 626 sh (11,900).

EXAMPLE 14

Preparation of 50 mg. tablets

| Per Tablet | | Per 10,000 Tablets |
|---|---|---|
| 0.050 gm. | 1,1'-[Iminobis(ethyleneimino)]-bis[5,8-dihydroxy-4-[[2-(2-hydroxyethylamino)ethyl]amino]-anthraquinone]tetrahydrochloride | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 1,1'-[iminobis(ethyleneimino)]bis[5,8-dihydroxy-4-[[2-(2-hydroxyethylamino)ethyl]amino]anthraquinone]tetrahydrochloride, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 15

Preparation of Parenteral Solution

In a solution of 700 ml. of propylene glycol and 200 ml. of water for injection is suspended 20.0 g. of 1,1'-[iminobis(ethyleneimino-ethyleneimino)]bis[5,8-dihydroxy-4-[[2-(2-hydroxyethylamino)ethyl]amino]anthraquinone]tetrahydrochloride with stirring. After suspension is complete, the pH is adjusted to 5.5 with hydrochloric acid and the volume is made up to 1000 ml. with water for injection. The formulation is sterilized, filled into 5.0 ampoules each containing 2.0 ml. (representing 40 mg. of drug) and sealed under nitrogen.

EXAMPLE 16

1,1'-(Ethylenediimino)bis[4-(2-aminoethyl)amino]-5,8-dihydroxyanthraquinonedihydrochloride A solution of 14.44 g. of ethylenediamine in 160 ml. of N,N,N',N'-tetramethylethylenediamine is deaerated by bubbling in nitrogen for 15 minutes with stirring. After addition of 41.94 g. of leuco 1,4,5,8-tetrahydroxyanthraquinone the mixture is stirred under nitrogen for one hour at 25° C., then stirred for another hour while heating with an oil bath at 48°–50° C. The mixture is allowed to cool, the solid is collected by filtration and washed with ethanol to give 28.25 g. of a green-black solid. This "leuco" adduct is oxidized with 19.77 g. of chloranil in 565 ml. of 2-methoxyethanol containing 14.4 ml. of 8 N ethanolic hydrogen chloride, as in Example 1. Collection of the solid by filtration and washing with tetrahydrofuran gives 29.66 g. of blue-black solid. This solid contains a water-soluble co-product, 1,4-bis(2-aminoethylamino)-5,8-dihydroxyanthraquinone dihydrochloride, which is removed by stirring with 800 ml. of water for 14 hours, centrifuging, then washing the solid with water by centrifugation. The insoluble, blue-black solid (6.8 g.) is the title compound. It is unmelted by 350° C.

We claim:
1. A compound selected from the group consisting of those of the formula:

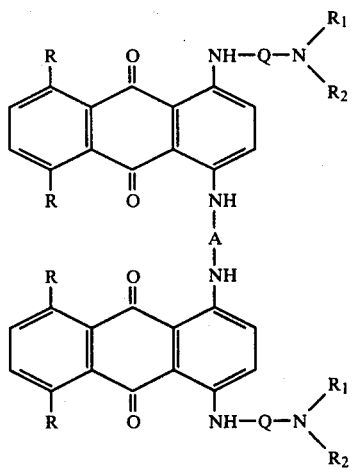 (I)

wherein Q is a divalent moiety selected from the group consisting of those of the formulae:

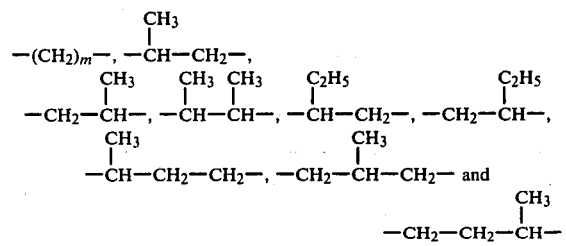

where m is an integer from 2 to 3, inclusive; A is $(CH_2)_nX(CH_2)_p$ where n and p may be the same or different and each may be an integer from 1 to 4 inclusive; X is selected from the group comprising

O, $(CH_2)_q$ where q is zero to 4,

where r is an integer from 2 to 6,

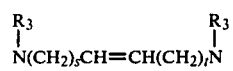

where s and t may be the same or different and each may be an integer from 1 to 3 and the olefin may be cis or trans, and

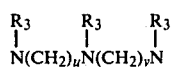

where u and v may be the same or different and each may be an integer from 2 to 5; R is hydrogen and hydroxy; $R_1$ and $R_2$ are each individually selected from the group consisting of hydrogen, alkyl having from 1 to 4 carbon atoms and monohydroxyalkyl having from 2 to 4 carbon atoms wherein the carbon atom alpha to the nitrogen atom may not bear a hydroxyl group, $R_3$ is hydrogen and lower alkyl $(C_1-C_3)$ and pharmaceutically acceptable acid-addition salts thereof.

2. A compound selected from the group consisting of those of the formula:

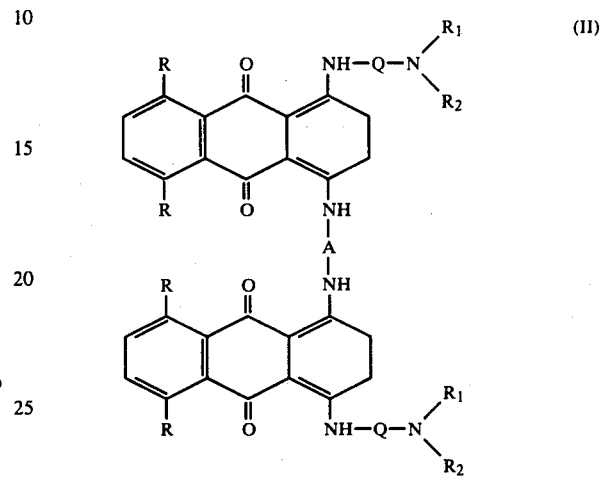 (II)

wherein Q is a divalent moiety selected from the group consisting of those of the formulae:

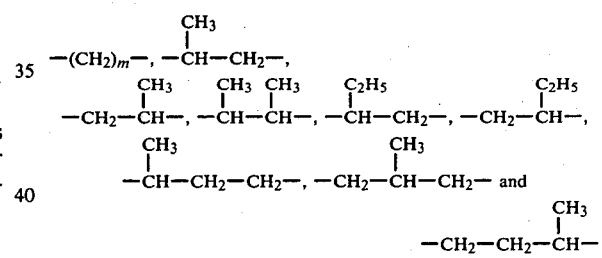

where m is an integer from 2 to 3, inclusive; A is $(CH_2)_nX(CH_2)_p$ where n and p may be the same or different and each may be an integer from 1 to 4 inclusive; X is selected from the group comprising

O, $(CH_2)_q$ where q is zero to 4,

where r is an integer from 2 to 6,

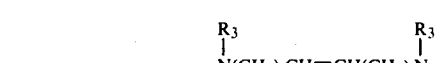

where s and t may be the same or different and each may be an integer from 1 to 3 and the olefin may be cis or trans, and

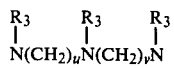

where u and v may be the same or different and each may be an integer from 2 to 5; R is hydrogen and hydroxy; $R_1$ and $R_2$ are each individually selected from the group consisting of hydrogen, alkyl having from 1 to 4 carbon atoms and monohydroxyalkyl having from 2 to 4 carbon atoms wherein the carbon atom alpha to the nitrogen atom may not bear a hydroxyl group, $R_3$ is hydrogen and lower alkyl ($C_1$–$C_3$).

3. The compound according to claim 1, 1,1'-[iminobis(ethyleneimino-ethyleneimino)]bis[5,8-dihydroxy-4-[[2-(2-hydroxyethylamino)ethyl]amino]anthraquinone]tetrahydrochloride.

4. The compound according to claim 1, 1,1'-[ethylenebis(iminoethyleneimino)]bis[5,8-dihydroxy-4-[[2-(2-hydroxyethylamino)ethyl]amino]anthraquinone]tetrahydrochloride.

5. The compound according to claim 1, 1,1'-(octamethylenediimino)bis[5,8-dihydroxy-4-[[2-(2-hydroxyethylamino)ethyl]amino]anthraquinone]dihydrochloride.

6. The compound according to claim 1, 1,1'-[iminobis(ethyleneimino)]bis[5,8-dihydroxy-4-[[2-(2-hydroxyethylamino)ethyl]amino]anthraquinone]trihydrochloride.

7. The compound according to claim 1, 1,1'-[trimethylenebis(iminoethyleneimino)]bis[5,8-dihydroxy-4-[[2-(2-hydroxyethylamino)ethyl]amino]anthraquinone[tetrahydrochloride.

8. The compound according to claim 1, 1,1'-[2-Butenylenebis(iminoethyleneimino)]bis[5,8-dihydroxy-4-[[2-(2-hydroxyethylamino)ethyl]amino]anthraquinone]tetrahydrochloride.

9. The compound according to claim 1, 1,1'-[tetramethylenebis(iminoethyleneimino]bis]5,8-dihydroxy-4-[[2-(2-hydroxyethylamino)ethyl]amino]anthraquinone]tetrahydrochloride.

10. The compound according to claim 1, 1,1'-[tetramethylenebis(iminotrimethyleneimino)]bis[5,8-dihydroxy-4-[[2-(2-hydroxyethylamino)ethyl]amino]anthraquinone]tetrahydrochloride.

11. The compound according to claim 1, 1,1'-[hexamethylenebis(iminoethyleneimino)]bis[5,8-dihydroxy-4-[[2-(2-hydroxyethylamino)ethyl]amino]anthraquinone]tetrahydrochloride.

12. The compound according to claim 1, 1,1'-[oxybis(tetramethyleneimino)]bis[5,8-dihydroxy-4-[[2-(2-hydroxyethylamino)ethyl]amino]anthraquinone]dihydrochloride.

13. The compound according to claim 1, 1,1'-[ethylenebis(iminoethyleneimino)]bis[5,8-dihydroxy-4-[(2-methylaminoethyl)amino]anthraquinone]tetrahydrochloride.

14. The compound according to claim 1, 1,1'-[ethylenebis(iminoethyleneimino)]bis[4-[[2-(2-hydroxyethylamino)ethyl]amino]anthraquinone]tetrahydrochloride.

15. The compound according to claim 2, leuco 1,1'-[iminobis(ethyleneimino-ethyleneimino)]bis[5,8-dihydroxy-4-[[2-(2-hydroxyethylamino)ethyl]amino]anthraquinone].

16. The compound according to claim 1, 1,1'-(ethylenediimino)bis[4-(2-aminoethyl)amino]-5,8-dihydroxyanthraquinone dihydrochloride.

* * * * *